United States Patent
El-Zehiry et al.

(10) Patent No.: US 11,610,316 B2
(45) Date of Patent: Mar. 21, 2023

(54) METHOD OF COMPUTING A BOUNDARY

(71) Applicant: Siemens Healthcare GmbH, Erlangen (DE)

(72) Inventors: Noha El-Zehiry, Plainsboro, NJ (US); Karim Amer, Cairo (EG); Mickael Sonni Albert Ibrahim Ide, Lawrence Township, NJ (US); Athira Jacob, Plainsboro, NJ (US); Gareth Funka-Lea, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 241 days.

(21) Appl. No.: 17/088,816

(22) Filed: Nov. 4, 2020

(65) Prior Publication Data

US 2021/0279884 A1    Sep. 9, 2021

Related U.S. Application Data

(60) Provisional application No. 62/986,188, filed on Mar. 6, 2020.

(51) Int. Cl.
*G06T 7/13* (2017.01)
*G06T 11/00* (2006.01)
(Continued)

(52) U.S. Cl.
CPC .............. *G06T 7/13* (2017.01); *A61B 8/0883* (2013.01); *A61B 8/14* (2013.01); *G06N 3/08* (2013.01);
(Continued)

(58) Field of Classification Search
None
See application file for complete search history.

(56) References Cited

U.S. PATENT DOCUMENTS

2007/0249912 A1* 10/2007 Tek .................. A61B 6/504
600/300
2018/0285535 A1* 10/2018 Zhu .................. G06F 16/3331
(Continued)

FOREIGN PATENT DOCUMENTS

CN    107516323 A  * 12/2017
CN    110189255 A  *  8/2019
(Continued)

OTHER PUBLICATIONS

Justin Liang, Raquel Urtasun; "End-to-End Deep Structured Models for Drawing Crosswalks", Proceedings of the European Conference on Computer Vision (ECCV), 2018, pp. 396-412.*
(Continued)

*Primary Examiner* — Jiangeng Sun
(74) *Attorney, Agent, or Firm* — Lempia Summerfield Katz LLC (57) ABSTRACT

The disclosure relates to a method for determining a boundary about an area of interest in an image set. The includes obtaining the image set from an imaging modality and processing the image set in a convolutional neural network. The convolutional neural network is trained to perform the acts of predicting an inverse distance map for the actual boundary in the image set; and deriving the boundary from the inverse distance map. The disclosure also relates to a method of training a convolutional neural network for use in such a method, and a medical imaging arrangement.

15 Claims, 7 Drawing Sheets

(51) Int. Cl.
   *G06T 7/00* (2017.01)
   *G06N 3/08* (2006.01)
   *G06V 10/25* (2022.01)
   *G06V 30/262* (2022.01)
   *A61B 8/14* (2006.01)
   *A61B 8/08* (2006.01)

(52) U.S. Cl.
   CPC .......... *G06T 7/0014* (2013.01); *G06T 11/003* (2013.01); *G06V 10/25* (2022.01); *G06V 30/274* (2022.01); *G06T 2200/24* (2013.01); *G06T 2207/10072* (2013.01); *G06T 2207/20081* (2013.01); *G06T 2207/20084* (2013.01); *G06T 2207/30048* (2013.01)

(56) References Cited

U.S. PATENT DOCUMENTS

| | | | | |
|---|---|---|---|---|
| 2018/0286023 A1* | 10/2018 | Zhu | .......................... | G06T 5/20 |
| 2019/0015059 A1* | 1/2019 | Itu | .......................... | G06F 16/285 |
| 2022/0156528 A1* | 5/2022 | Borse | .................... | G06V 10/765 |

FOREIGN PATENT DOCUMENTS

| | | | | | | |
|---|---|---|---|---|---|---|
| CN | 110297223 | A | * | 10/2019 | | |
| CN | 110599500 | A | * | 12/2019 | | |
| CN | 106203432 | B | * | 1/2020 | .......... | G06K 9/3233 |
| CN | 110717518 | A | * | 1/2020 | | |
| CN | 105224942 | B | * | 2/2020 | .......... | G06K 9/4652 |
| CN | 110930427 | A | * | 3/2020 | ............ | G06T 7/149 |
| CN | 112274164 | A | * | 1/2021 | | |
| WO | WO-2009101560 | A2 | * | 8/2009 | ............ | G06T 5/003 |
| WO | 2021032325 | A1 | | 2/2021 | | |

OTHER PUBLICATIONS

Phlipp Henzler, Volker Rasche, Timo Ropinski, Tobias Ritschel, "Single-image Tomography: 3D Volumes from 2D Cranial X-Rays", arXiv:1710.04867v3 [cs.GR] Nov. 28, 2018.*

Kiriakos N. Kutulakos, a Theory of Shape by Space Carving, International Journal of Computer Vision 38(3), 199-218, 2000.*

Badrinarayanan, Vijay, Alex Kendall, and Roberto Cipolla. "Segnet: A deep convolutional encoder-decoder architecture for image segmentation." IEEE transactions on pattern analysis and machine intelligence 39.12 (2017): 2481-2495.

Chen, Liang-Chieh, et al. "Deeplab: Semantic image segmentation with deep convolutional nets, atrous convolution, and fully connected crfs." IEEE transactions on pattern analysis and machine intelligence 40.4 (2017): 834-848.

He, Kaiming, et al. "Deep residual learning for image recognition." Proceedings of the IEEE conference on computer vision and pattern recognition. 2016. pp. 770-778.

Liao, Haofu, et al. "More knowledge is better: Cross-modality volume completion and 3d+ 2d segmentation for intracardiac echocardiography contouring." International Conference on Medical Image Computing and Computer-Assisted Intervention. Springer, Cham, 2018. pp. 1-9.

Long, Jonathan, Evan Shelhamer, and Trevor Darrell. "Fully convolutional networks for semantic segmentation." Proceedings of the IEEE conference on computer vision and pattern recognition 2015. pp. 3431-3440.

Lorensen, William E., and Harvey E. Cline. "Marching cubes: A high resolution 3D surface construction algorithm." ACM siggraph computer graphics 21.4 (1987): 163-169.

Osher, S. et. al., "Level Set Methods and Dynamic Implicit Surfaces", Springer-Verlag, 2002. pp. 1-288.

Ronneberger, Olaf, Philipp Fischer, and Thomas Brox. "U-net: Convolutional networks for biomedical image segmentation." International Conference on Medical image computing and computer-assisted intervention. Springer, Cham, 2015. pp. 234-241.

Sethian, James Albert. Level set methods and fast marching methods: evolving interfaces in computational geometry, fluid mechanics, computer vision, and materials science. vol. 3. Cambridge university press, 1999; viewable online at: https://math.berkeley.edu/~sethian/2006/Publications/Book/2006/book_1999.html.

Zhang, T. Y., and Ching Y. Suen. "A fast parallel algorithm for thinning digital patterns." Communications of the ACM 27.3 (1984): 236-239.

* cited by examiner

FIG 1

M - 3D volume
30 - Obtaining 3D volume
31 - Identify surface boundary
32 - Feed blurred boundary mesh and 3D volume into convolutional neural network
1 - Convolutional neural network

M   3D volume
D   Identify area of interest
E   Feed 3D volume and information identifying area of interest into model
F   Refining boundary of surface inclosing area of interest
1   Convolutional neural network

METHOD OF COMPUTING A BOUNDARY

The present patent document claims the benefit of U.S. Provisional Patent Application No. 62/986,188, filed Mar. 6, 2020, which is hereby incorporated by reference.

TECHNICAL FIELD

The disclosure relates to a method of computing a boundary of an area of interest in an image set, a method of training a convolutional neural network, and a medical imaging arrangement.

BACKGROUND

The disclosure addresses the problem of how to accurately delineate the boundary of an object, (e.g., the boundary about an area of interest), from one or more images of an imaging modality. The term "object" used herein should be understood to mean a distinct region or area of interest seen in an image or image volume. In the case of medical images, the area of interest may belong to an organ, an anomaly, a blood vessel, etc.

To delineate the boundary of an object in an image obtained from a 2D imaging modality, it is known to deploy deep learning image-to-image segmentation models with the aim of producing a segmentation mask. The area of interest is segmented from the remainder of the image contents, and a corresponding segmentation mask is computed. The object boundary, (e.g., the boundary of the area of interest), is then computed as the edge of the segmentation mask. In this type of approach, the area of the segmented region is first computed before the enclosing boundary may be determined. Similarly, to delineate the surface boundary of an object in an image volume obtained from a 3D imaging modality, it is known to deploy deep learning volume-to-volume segmentation models that process the volume images with the aim of producing segmentation masks. In this 3D approach, the area of interest is segmented from each image in the set of images so that the volume of the segmented region may be computed, and its object boundary may then be computed as the edge of a 3D segmentation mask, using a suitable algorithm such as the marching cubes algorithm. Again, this known approach effectively computes an enclosed volume, from which the surface boundary may then be derived. For the known methods to produce reliable results, the neural networks may be trained on dense input, e.g., an input with many image slices and/or high resolution. This adds to the overall cost of the conventional approach.

SUMMARY AND DESCRIPTION

It is therefore an object of the disclosure to provide an improved way of accurately determining such a boundary.

This object is achieved by the method of computing a boundary about an area of interest in an image set, by the method of training a convolutional neural network, and by the medical imaging arrangement. The scope of the present disclosure is defined solely by the appended claims and is not affected to any degree by the statements within this summary. The present embodiments may obviate one or more of the drawbacks or limitations in the related art.

According to the disclosure, the method provides a way of computing a boundary about an area of interest seen in an image set obtained from an imaging modality, e.g., a medical imaging modality. The method includes processing the image set in a deep learning convolutional neural network that has been trained to perform the acts of predicting an inverse distance map for a boundary that may be seen in the image set; and to subsequently derive the boundary about the area of interest, (e.g., the boundary delineation), from the predicted inverse distance map. An advantage of the method is that it enables prediction of the boundary of a cavity or other surface even in the absence of information about the space enclosed by the boundary. The disclosure is therefore highly suited to identifying boundaries from single images or sparse image volumes. This is made possible by the insight of training the convolutional neural network on a non-binary ground truth, as will be explained below.

As described above, conventional image-to-image or volume-to-volume segmentation methods that aim to describe a boundary use binary segmentation masks to train a network. A binary segmentation mask is a set of "true" values for any point inside the area of interest and "false" values for all points outside the area of interest. The conventional approach to training a neural network on segmentation masks was developed largely on account of numerical stability, because training a neural network using boundaries that abruptly change from "true" to "false" has been found to be numerically unstable. In the conventional approach, a boundary is extracted (e.g., by the trained neural network) as the edge of the binary mask, which therefore is developed first. The reason for identifying a boundary about an area of interest is because the boundary may assist in arriving at a diagnosis, for example, by allowing a clinician to identify the presence or absence of anomalies. As indicated above, the conventionally deployed neural networks may be trained with high-resolution images and/or dense 3D image volumes in order to arrive at a satisfactory level of accuracy. As disclosed herein, it is possible to obtain an accurate depiction of an object (such as a cavity or chamber) by focusing only on the boundaries of the object, instead of on the object's binary segmentation mask.

According to the disclosure, the method of training such a convolutional neural network includes: annotating an image set to identify a boundary about an area of interest; replicating an inverse distance map of the boundary to give a non-binary ground truth for the convolutional neural network; applying the convolutional neural network to the image set and the associated ground truth to predict an inverse distance map approximating the ground truth; and repeating the annotating, the replicating, and the applying until the surface boundary prediction is performed to a desired level of accuracy.

The convolutional neural network may be configured to perform semantic image segmentation. In one example, the convolutional neural network is U-Net, but any other semantic segmentation architecture (such as a residual neural network, SegNet, DeepLab etc.) may be implemented. In the following, without restricting the disclosure in any way, the convolutional neural network is assumed to be U-Net or an equivalent.

According to the disclosure, the medical imaging arrangement includes: an imaging module configured to provide an image set; a processing unit configured to perform boundary prediction when the trained convolutional neural network loaded into a memory of the processing unit; and a user interface configured at least to display the inferred boundary in the context of the image set.

The units or modules of the medical imaging arrangement mentioned above may be completely or partially realized as software modules running on a processor of a control unit. A realization largely in the form of software modules may have the advantage that applications already installed on an existing system may be updated, with relatively little effort, to install and run the acts of the method to obtain a boundary about an area of interest in an image set. The object is also achieved by a computer program product with a computer program that is directly loadable into the memory of a control unit of a medical imaging arrangement, and which includes program units to perform the acts of the method to infer a boundary about an area of interest in an image set when the program is executed by the control unit.

Features of different claim categories may be combined as appropriate to give further embodiments not described herein.

In the following, without restricting the disclosure in any way, it may be assumed that an image is a monochrome intensity image, i.e. the image is "black and white".

In the context of the disclosure, a boundary shall be understood as a set of points defining a contour about a region of interest. A "two-dimensional boundary" shall be understood to mean an edge contour in a 2D image, (e.g., the contour of an organ, the contour of a cavity in an organ, etc.). For example, a 2D boundary may be an inner or outer edge of an organ imaged by an ultrasound modality. The terms "two-dimensional" and "2D" are synonymous and are used interchangeably herein. Similarly, a "three-dimensional surface boundary" shall be understood to mean a surface in a 3D image volume, (e.g., the surface contour of an organ, the surface contour of a cavity in an organ, etc.). For example, a 3D boundary may be an inner surface or outer surface of an organ imaged by a 3D imaging modality such as intracardiac echocardiography. An example of such a surface might be the interior surface of a chamber of the heart. The terms "three-dimensional" and "3D" are synonymous and are used interchangeably herein.

Depending on the content of the image set, the boundary that is computed by the convolutional neural network may be an "open" or partial boundary (i.e., not closed). In other words, the method works well for incomplete or partial boundaries. This is in contrast to conventional segmentation methods, which suffer from the limitation that an open or partial boundary cannot be represented by a binary mask. The method overcomes this limitation. The inventors have not been able to identify any prior publication in the field of segmentation that would suggest a deep learning approach to identifying partial or open boundaries.

There are various ways of mathematically representing such a boundary. For example, a surface boundary may be represented implicitly by the zero-level set of a distance map representation. The problem addressed by the disclosure is how to obtain such a distance map for a boundary in an image set without having to compute the area or volume contained by the boundary, e.g., without having to compute the area contained by the boundary about the area of interest in a 2D image, or without having to compute the volume contained by the surface boundary about the area of interest in a 3D image volume.

In the following, unless indicated otherwise, the method may be explained using 3D volumetric images obtained from an intracardiac echocardiography (ICE) imaging modality. Other suitable 3D imaging modalities may be X-ray, magnetic resonance imaging (MRI), computed tomography (CT), Poisson emission tomography (PET), etc., and it shall be understood that the disclosure is also applicable to non-medical imaging modalities.

It shall be noted that the image set used by the method does not need to be obtained from a 3D imaging modality, and may instead be a sparse 3D volume that is generated from a plurality of image slices from a 2D imaging modality such as 2D intracardiac echocardiography. The 3D volume may be dense, but the disclosure provides very satisfactory results even using a sparse 3D volume as input, (e.g., a sparse 3D volume compiled from a plurality of 2D image slices).

In a method, a convolutional neural network (CNN) is trained with a non-binary ground truth representing a surface boundary, e.g., by implementing a function that mimics a distance map. In the method, the convolutional neural network is initially trained using many such ground truths. By training the CNN directly on the boundary map, the CNN learns a regression function that provides the distance from the boundary as an output, e.g., a distance map. In the context of the disclosure, the terms "distance map" and "boundary map" may be regarded as synonyms and may be used interchangeably, and the term "boundary mesh" may also be used in the context of a 3D surface boundary.

The network architecture may be a U-Net with four levels. Each level includes an encoder block with several convolution filters and a decoder block with several deconvolution filters. For example, on the encoder side, each encoder block may be followed by a 2×2×2 average pooling function. On the decoder side, each decoder block is preceded by a bilinear upsampling function. A copy-and-concatenate function links each encoder block of the first three levels to the corresponding decoder block. The number and size of the convolution/deconvolution filters may be adjusted as appropriate. For example, the number of filters in the first, second, third, and fourth layers may be 32, 64, 128, and 196, respectively. Each filter is of size 3×3×3.

In an embodiment, a ground truth is determined by obtaining a known boundary (e.g., annotated from a medical image volume by an expert) and subjecting the annotated boundary to blurring by a Gaussian filter, which provides a favorable approximation to an inverse distance map.

For a 2D boundary, an inverse distance map I(p) may be a negative exponential transformation function, for example:

$$I(p) = e^{-\frac{D(p)}{\alpha}} \quad (1)$$

In equation (1), $p \in R^2$ is a point in the image, a is a normalization parameter that is empirically defined, and D(p) is the distance to the contour boundary defined as:

$$D(p) = \min \|p, q\| \forall q \in \Gamma \quad (2)$$

In equation (2), q is any point on the 2D boundary $\Gamma$. For a 3D boundary, e.g., a surface boundary, an inverse distance map I(M) may be a suitable Gaussian filter, for example:

$$I(v) = \frac{1}{(2\pi)^{\frac{3}{2}}\sigma^3} e^{-\frac{\min|v-v_s|^2}{2\sigma^2}} \quad \forall v_S \in S \quad (3)$$

In equation (3), $\sigma$ is the standard deviation used, v is any voxel in the image space, and $v_S$ is any voxel on the surface boundary S. The value of $\sigma$ may be used to control the smoothness of the transition (e.g., the level of blur) between the boundary and the other points in the 3D image volume. In a further embodiment, the $\sigma$ parameter for the Gaussian filter (or a parameter of any function used to compute a distance to the object boundary) is learned as part of the training process.

The values of the distance to the boundary may span a large range depending on the image size and the size of the boundary. Therefore, the model may be trained on a representation that compresses the range of distances to ]0,1].

In the method, the replication of an inverse distance map is used as a ground truth to train the model. In other words, the model is trained to learn this representation of an inverse distance map. The model may be trained using a plurality of such inverse distance map replications. A high degree of accuracy of the model may be obtained by training with at least several hundred ground truths.

The act of training may minimize the mean squared error between each ground truth and the corresponding boundary map predicted by the model. There may be a single object of interest, for example, a clinician wishes to obtain the boundary for a specific chamber or vessel. For a single object of interest in a 2D image, the mean squared error loss function may be expressed as:

$$\frac{1}{M}\sum_{p=1}^{M}|I_k(p) - \hat{I}_k(p)| \quad (4)$$

where M is the number of pixels in the 2D image.

To segment multiple objects simultaneously from a 2D image, the loss function may be generalized to include the errors from all detected boundaries. For K objects of interest in the image, the loss function of (xx) is modified to:

$$\frac{1}{KM}\sum_{K=1}^{K}\sum_{p=1}^{M}|I_k(p) - \hat{I}_k(p)| \quad (5)$$

For a single object of interest in a 3D image volume, the mean squared error loss function may be expressed as:

$$\frac{1}{M}\sum_{p=1}^{M}(I_k(v) - \hat{I}_k(v))^2 \quad (6)$$

In equation (6), M is the number of voxels in the 3D volume.

If there are multiple objects of interest in an image or in a volume, the corresponding loss function may be modified as follows:

$$\frac{1}{KM}\sum_{K=1}^{K}\sum_{p=1}^{M}(I_k(v) - \hat{I}_k(v))^2 \quad (7)$$

Here, the loss function is generalized to include errors from all detected boundaries in order to segment multiple objects simultaneously.

After supervised training is complete, the model may be applied to predict or infer any boundary from a 2D image or any three-dimensional surface boundary in an image volume. In inference mode, the model predicts a distance map for the boundary of interest. The predicted inverse distance map effectively provides a blurred or "fuzzy" version of the actual boundary. The boundary may be derived from the predicted inverse distance map by first thresholding the blurred inverse distance map to obtain a binary boundary, which may be visualized as a thick line (2D case) or a thick surface (3D case). In a subsequent act, the binary boundary is skeletonized to extract the medial axis of the binary boundary. The result is a thinned boundary that accurately represents the actual contour of the area of interest. The thickness of the thinned boundary may be as small as one pixel (2D case) or one voxel (3D case).

The approach may be used to infer a partial or complete boundary from a 2D image. In this case, the architecture of the CNN is based on two-dimensional filters, and the ground truths used to train the CNN may be simple contours (e.g., open or closed), which may be obtained by manual annotation of 2D images.

BRIEF DESCRIPTION OF THE DRAWINGS

Other objects and features of the present disclosure will become apparent from the following detailed descriptions considered in conjunction with the accompanying drawings. It is to be understood, however, that the drawings are designed solely for the purposes of illustration and not as a definition of the limits of the disclosure.

In the diagrams, like numbers refer to like objects throughout. Objects in the diagrams are not necessarily drawn to scale.

DETAILED DESCRIPTION

The diagrams illustrate exemplary embodiments using images of a 3D Intracardiac Echocardiography (ICE) image volume, but it shall be understood that the method may be deployed to infer a boundary about a region of interest in a 2D image. Furthermore, it shall be understood that the method may be deployed for other imaging modalities. For example, a set of images from a 2D imaging modality may be assembled into a sparse 3D volume for use as an input to the training network. A 3D volume is considered sparse in the case of incomplete sampling of all voxel locations. While the following diagrams may only show images in the plane of the page, it shall be understood that the method is performed on a 3D volume and that any image shown in a diagram is only one "slice" of a 3D volume.

Figure 1:
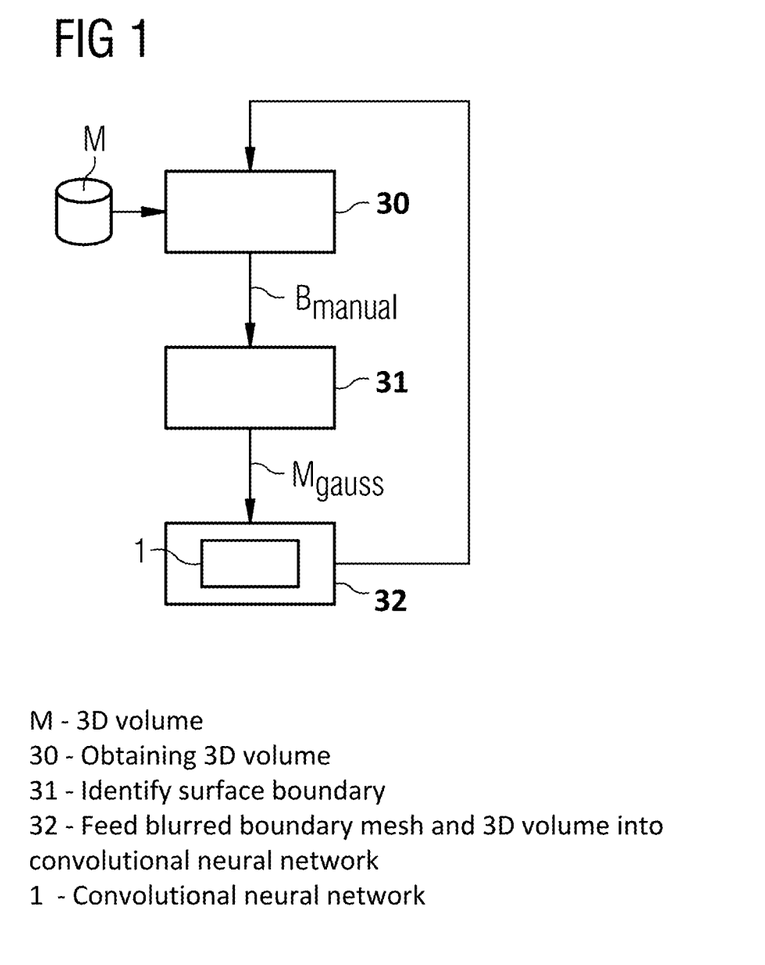
FIG. 1 illustrates an example of a training stage of the method.

FIG. 1 illustrates stages in a training stage of the method. In a first stage 30, a 3D volume M is obtained for an imaging modality such as ICE. A boundary mesh $B_{manual}$ is identified for a surface boundary, for example an interior or exterior surface of an organ, the interior surface of a blood vessel, etc. This act may be done by a trained expert. In act 31, the surface boundary $B_{manual}$ thus identified is then subject to Gaussian filtering as explained above, with a suitable choice of standard deviation a. In act 32, the blurred boundary mesh $M_{gauss}$ and the 3D volume M are then fed into a suitable convolutional neural network 1, which learns to infer an inverse distance map $M_{infer}$ while minimizing the difference between the input ground truth $M_{gauss}$ and the inferred distance map $M_{infer}$. Training is repeated for a plurality of ground truths $M_{gauss}$ until a desired accuracy is obtained.

Figure 2:
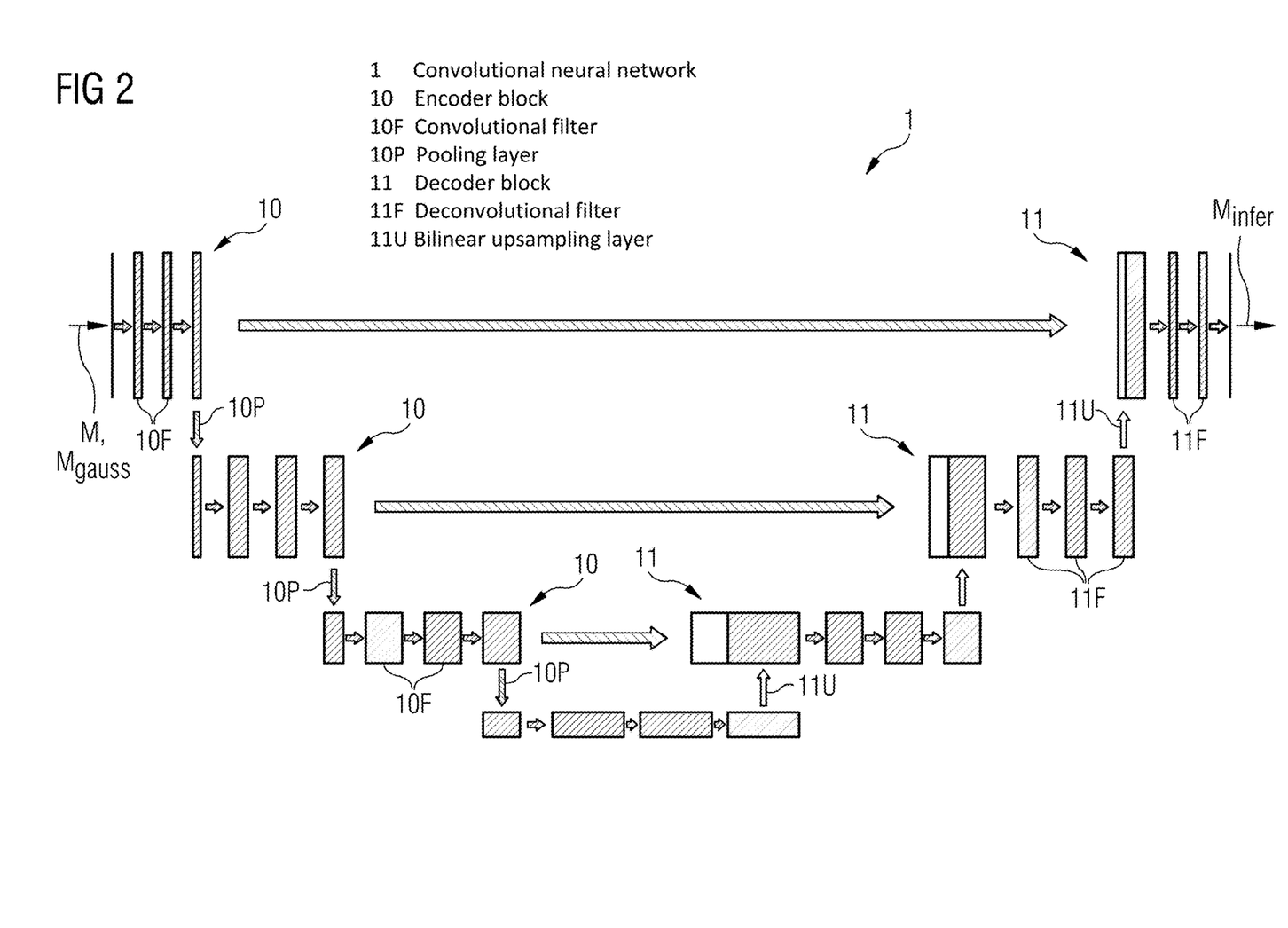
FIG. 2 shows a simplified block diagram of an example of a convolutional neural network used in the method.

FIG. 2 illustrates an exemplary embodiment of a U-Net architecture used to train a model to identify a 3D boundary. The convolutional neural network 1 includes four encoder blocks 10 and four decoder blocks 11. Each encoder block 10 includes several convolution filters 10F, and each decoder block 11 includes several deconvolution filters 11F. The filters 10F, 11F may vary in number. For example, the first, second, third and fourth blocks may implement 32, 64, 128, and 196 filters, respectively. Each filter 10F, 11F may be 3×3×3 in size. Each encoder block 10 is followed by a 2×2×2 average pooling layer 10P, while each decoder block 11 is preceded by a bilinear upsampling 11U layer.

As explained above, this convolutional neural network 1 is trained on a non-binary ground truth representation, (e.g., non-binary representations of boundaries are used to train the convolutional neural network).

In an exemplary embodiment, the ground truth is an inverse distance map. This stage of the training is illustrated with FIG. 3. A 3D image volume is presented to a user (e.g. in the display of a graphical user interface or GUI). The user identifies a structure, (e.g., a heart cavity or cardiac chamber), and annotates the 3D volume with a boundary mesh $B_{manual}$ of the structure. The annotated boundary mesh $B_{manual}$ may be regarded as a set of points in Cartesian space, (e.g., a distance map as expressed by equation (1)). The boundary mesh is then blurred by passing it through a Gaussian filter as explained above with the aid of equation (2). The purpose of the Gaussian filtering is to mimic or replicate an inverse distance map for the boundary. A replication of the inverse distance map is used as a ground truth for training.

Figure 3:
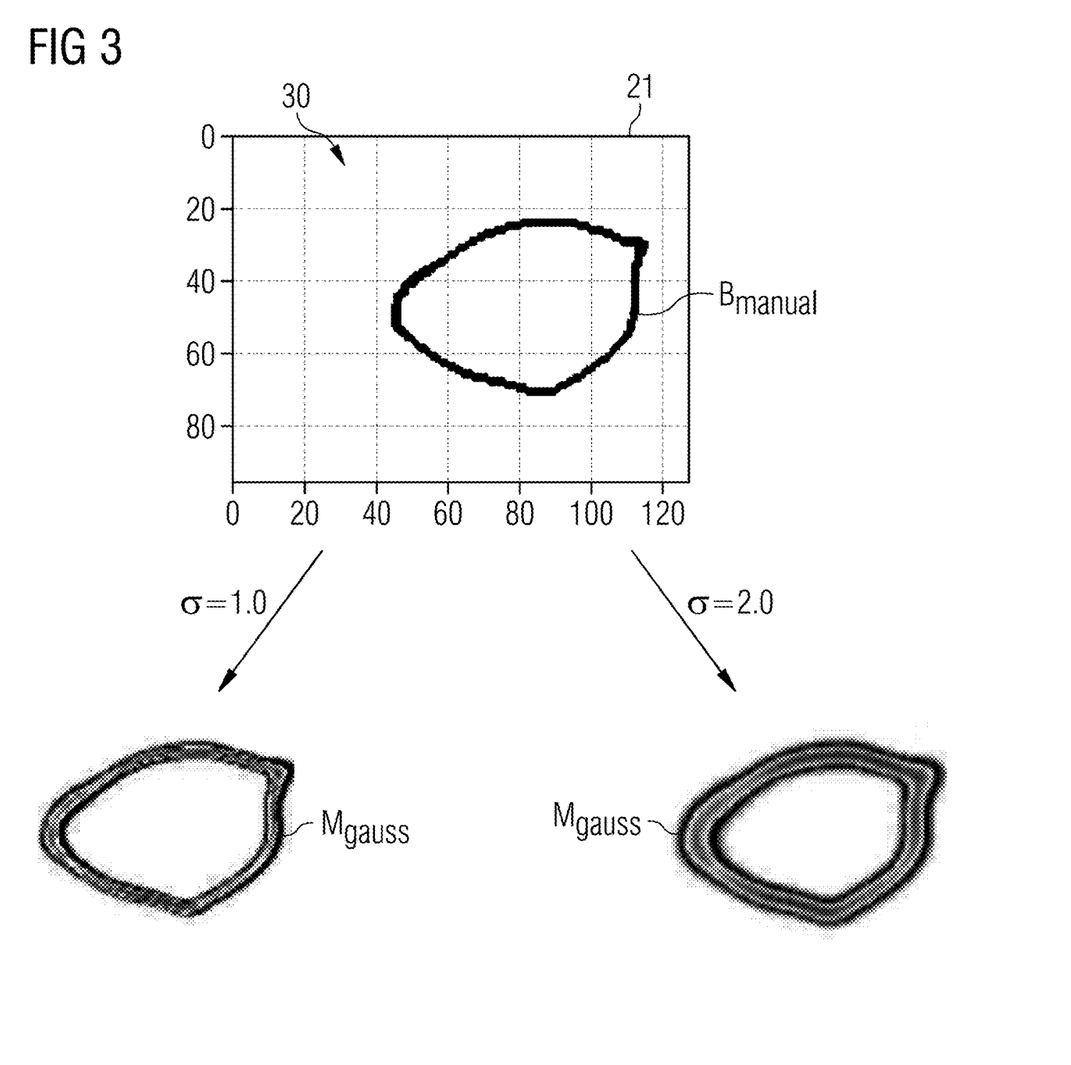
FIG. 3 is an example of a 2D representation of the development of a replication of an inverse distance map.
Figure 5:
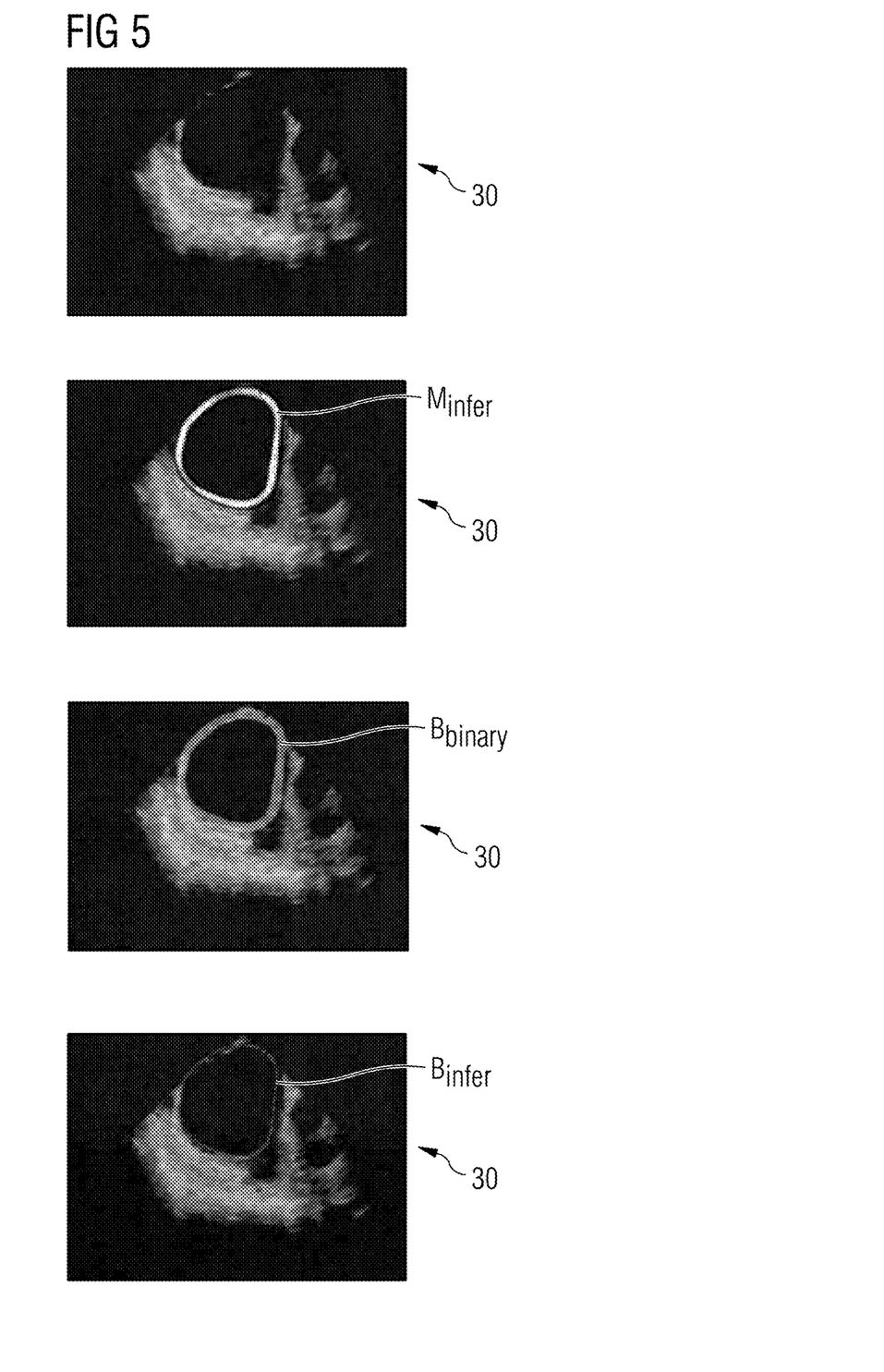
FIG. 5 is an example of a 2D representation of stages in the method.
Figure 7:
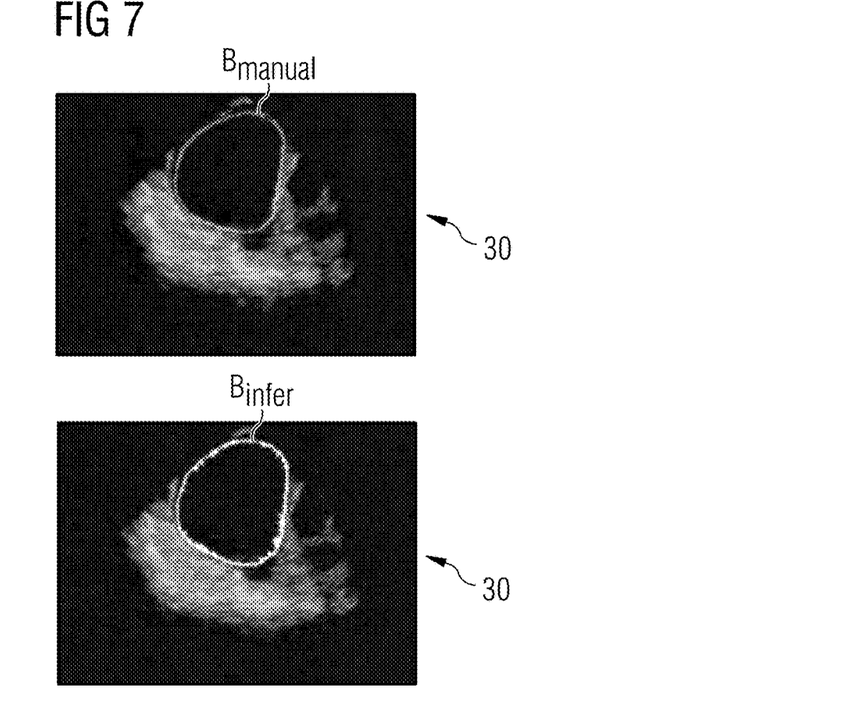
FIG. 7 compares an exemplary outcome of the method with a corresponding manual annotation.

The drawing indicates an image 30 shown in the display 21, and any such image may be assumed to be similar to the 3D ICE images shown in FIG. 5 and FIG. 7. The drawing shows a slice through the manually annotated boundary mesh $B_{manual}$; a slice through a filtered boundary mesh $M_{gauss}$ after blurring by a Gaussian filter with σ=1; and a slice through a filtered boundary mesh $M_{gauss}$ after blurring by a Gaussian filter with σ=2. The value of σ determines the smoothness of the filtered boundary.

The task of the convolutional neural network 1 of FIG. 2 is to learn how to identify a surface boundary without first computing the enclosed volume. The forward pass of the convolutional neural network 1 estimates the 3D boundary through a 3D distance map. The network training aims to minimize a loss function between the predicted distance map $M_{infer}$ and the ground truth distance map $M_{gauss}$. As explained above, a suitable choice of loss function may be the mean squared error of equation (3) above. The convolutional neural network 1 is trained using multiple ground truths. A high degree of accuracy of the model may be obtained by training with several hundred ground truths. This compares favorably with the conventional methods, which may require several thousand annotated segmentation masks in order to train a neural network to a comparable level of accuracy.

After training is complete, the model 1 may be applied to detect or infer boundary surfaces in a 3D image volume. In inference mode, the model 1 predicts a distance map $M_{infer}$ from the surface boundary about an area of interest, after which thresholding and skeletonization acts are performed to arrive at the predicted surface boundary.

Figure 4:
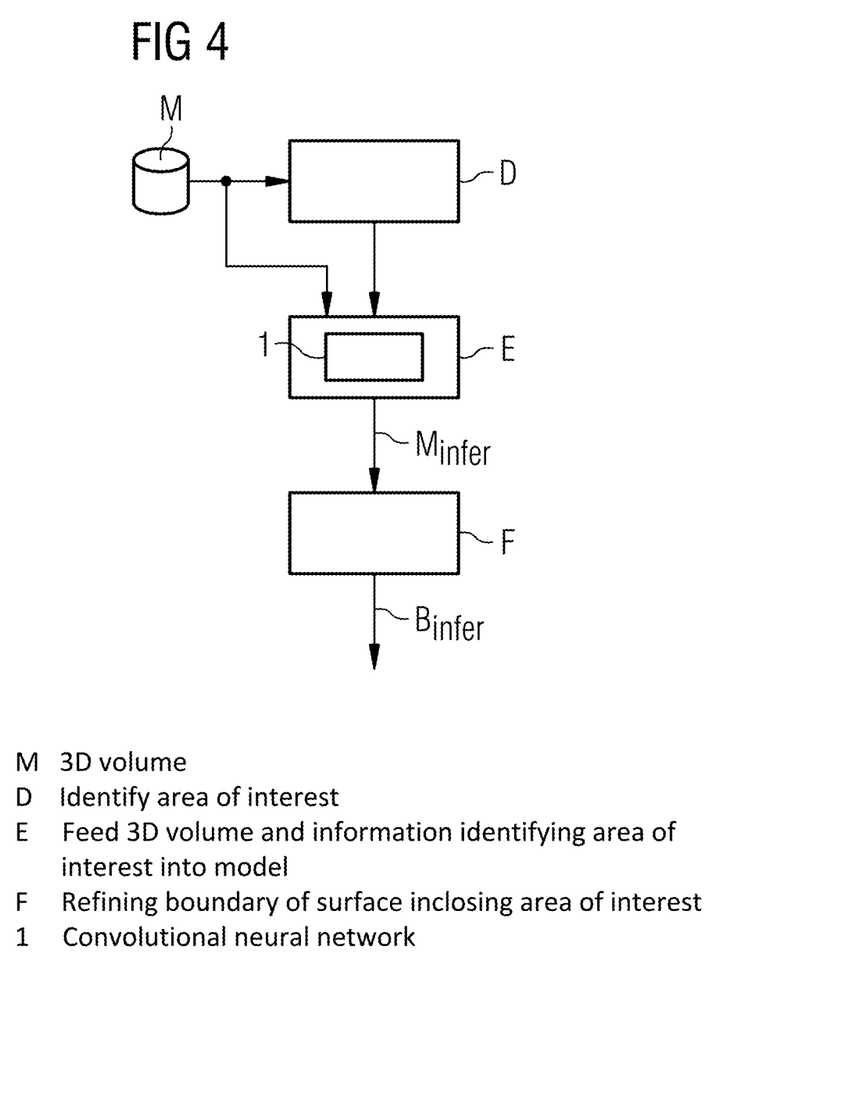
FIG. 4 illustrates an example of a workflow when applying the method to determine a 3D surface boundary.

FIG. 4 illustrates a workflow when applying the method to determine a 3D surface boundary. Here, an image volume M is obtained, for example, an image volume of an ICE procedure. In act D, the clinician identifies an area of interest, for example, a chamber or a blood vessel of the heart. It may be sufficient for the clinician to position a cursor over the area of interest, (e.g., "inside" the cavity shown on the monitor), so that the coordinates of the cursor relative to the image may be noted. Of course, the area of interest may be identified by the clinician or user in any suitable manner. In act E, the 3D volume M and any information identifying the area of interest are then fed to the model 1 which has been trained as explained above and illustrated in FIG. 2. The model 1 infers the boundary $M_{infer}$ of the surface enclosing the area of interest and this inferred boundary is then refined in act F by thresholding and skeletonization to obtain a 3D surface boundary $B_{infer}$ which may then be shown to the user, for example, by overlaying the inferred boundary onto the original image data.

FIG. 5 is a 2D representation of stages in the method and shows a 2D "slice" 30 of a 3D ICE volume to illustrate some of the main method acts. The area of interest is the large cavity which may be seen in the upper region of the image 30, in this case, the left atrium of the heart. It is the surface of the 3D cavity which is of interest to the clinician.

The trained convolutional neural network 1 described in FIG. 2 above predicts a 3D inverse distance map $M_{infer}$ for the cavity surface. The predicted 3D inverse distance map $M_{infer}$ is visualized here by projecting it onto the 2D image slice 30. The thickness of the 3D inverse distance map $M_{infer}$ may be controlled by choosing a suitable value of standard deviation σ in equation (2).

The inverse distance map $M_{infer}$ is then thresholded to obtain a binary boundary $B_{binary}$, (e.g., a set of values that either belong to the boundary or do not belong to the boundary). An exemplary result of thresholding the distance map $M_{infer}$ is superimposed on the image 30 and shows a band $B_{binary}$ representing the values that are deemed to belong to the boundary. The "thickness" of the binary boundary $B_{binary}$ depends on the choice of threshold, and a threshold value may be chosen that will provide a non-fragmented boundary.

In a final stage, the surface boundary $B_{infer}$ is refined by performing a skeletonization act (or "thinning") on the binary boundary $B_{binary}$ to extract the medial axis. The 3D surface boundary $B_{infer}$ may then be presented to the user by a suitable graphics program. Alternatively, as indicated here, a slice through the surface boundary $B_{infer}$ may be superimposed on the corresponding slice 30 of the 3D volume and shown to the user. Once the 3D surface boundary $B_{infer}$ is established for the area of interest, the user may interact with the imaging modality to alter the viewing angle, and the image presented on the monitor is continually updated to show the correct slice through the surface boundary $B_{infer}$.

Figure 6:
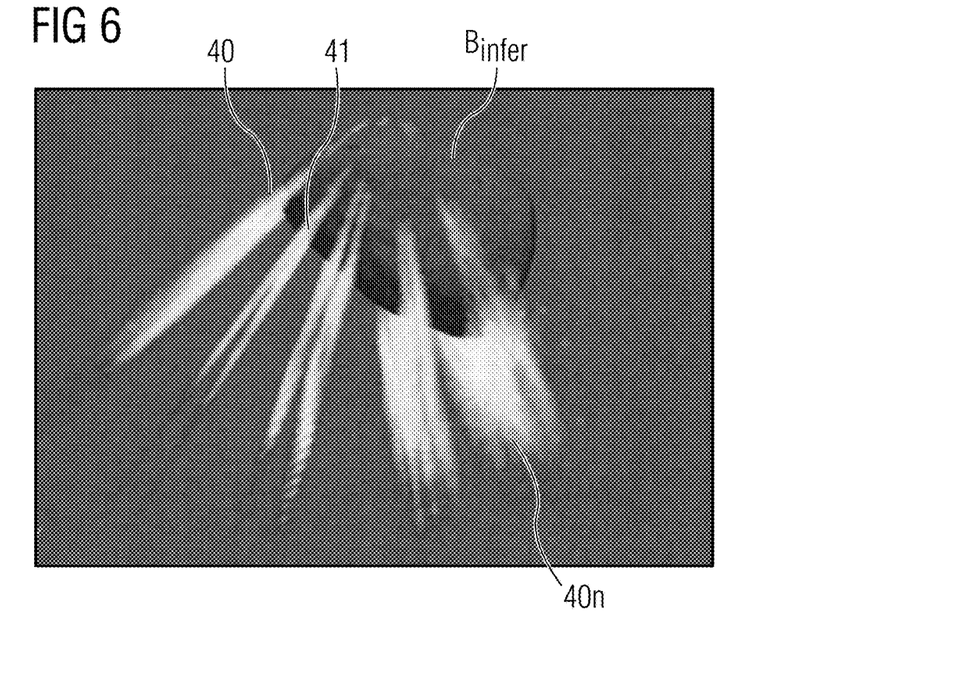
FIG. 6 is an example of a 2D projection of an exemplary outcome of the method.

FIG. 6 is a 2D projection of an exemplary outcome of the method. The diagram indicates various planes 40, ..., 40n, each of which corresponds to a 2D image from which a sparse 3D volume is compiled. Even though the 3D volume contains relatively little information, the method is able to identify a surface boundary $B_{infer}$ for a cavity in an organ imaged using a modality such as ICE. To provide such a 3D volume when only 2D images are available, a suitable form template (e.g., from a library of shapes) may be chosen which best fits a boundary shown in the images. A rough mesh may be derived from the template, and this rough mesh may then be used in a training act for the neural network.

FIG. 7 illustrates the effectiveness of the method. The diagram shows a 2D slice 30 of a 3D ICE volume. The upper part of the diagram shows a 2D projection of a 3D ground truth boundary mesh $B_{manual}$ for the left atrium, manually annotated in the image 30 by an expert. This ground truth $B_{manual}$ is used in a training act to train the convolutional neural network 1 of FIG. 2. The lower part of the diagram shows a 2D projection of the 3D left atrium boundary surface $B_{infer}$ as predicted or inferred by the convolutional neural network 1.

Figure 8:
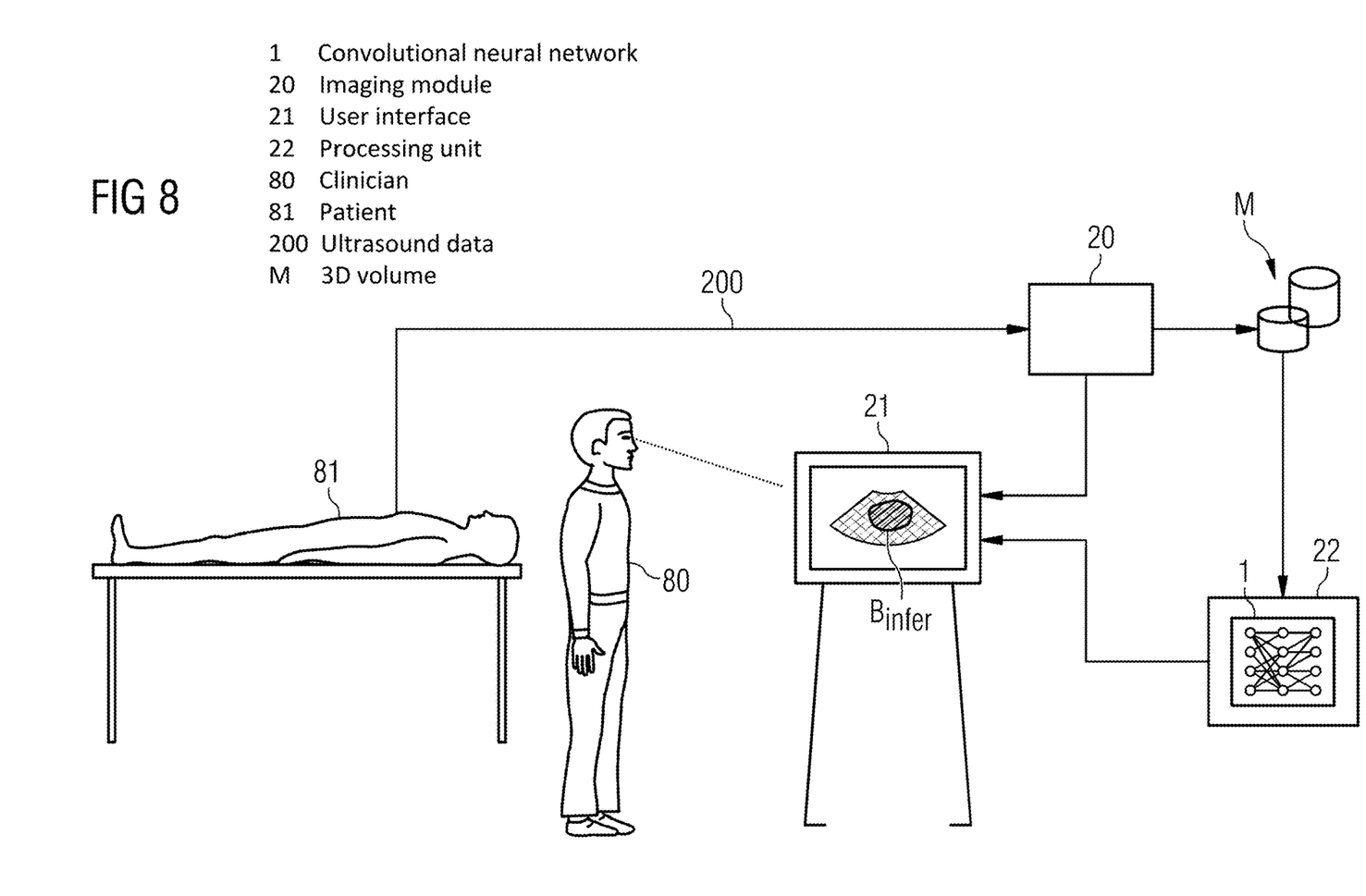
FIG. 8 shows an embodiment of the medical imaging arrangement.

FIG. 8 shows an exemplary medical imaging arrangement 2 with an imaging module 20, in this case a 3D echocardiography device configured to provide a 3D ICE volume M from ultrasound data 200 received from an ultrasound probe. After insertion of a catheter carrying an intracardiac ultrasound probe, a clinician 80 may view the interior regions of the heart on a display of a user interface 21, for example, in order to arrive at a diagnosis for the patient 81. This exemplary embodiment of the medical imaging arrangement 2 includes a processing unit 22 that is configured to infer a 3D surface boundary $B_{infer}$ for any area of interest in the 3D ICE volume M. The processing unit 22 includes a convolutional neural network 1 trained as explained above. The user interface 21 may display the computed or inferred three-dimensional surface boundary $B_{infer}$ in the context of the 3D ICE volume. Because the CNN 1 may very quickly infer a 3D surface boundary for any cardiac structure, the clinician 80 may view the inferred surface "live" during the ICE imaging procedure. The various components are shown separately in this exemplary schematic, but it shall be understood that the imaging module 20, user interface 21 and processing unit 22 may be realized collectively as a stand-alone unit.

Although the present disclosure has been discussed in the form of certain embodiments and variations thereon, it will be understood that numerous additional modifications and variations may be made thereto without departing from the scope of the disclosure. For example, when inferring a boundary from a 2D image, the architecture of the CNN is based on two-dimensional filters, and the ground truths used to train the CNN may be simple contours (e.g., open or closed) obtained by manual annotation of 2D images.

For the sake of clarity, it is to be understood that the use of "a" or "an" throughout this application does not exclude a plurality, and "comprising" does not exclude other acts or elements. The mention of a "unit" or a "module" does not preclude the use of more than one unit or module.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the disclosed embodiments, the disclosure is not limited to the disclosed examples. Other variations may be deducted by those skilled in the art without leaving the scope of protection of the claimed disclosure.

The invention claimed is:

1. A method of determining a boundary about an area of interest in an image set, the method comprising:
   obtaining the image set from an imaging modality; and
   processing the image set in a convolutional neural network,
   wherein the convolutional neural network has been trained through:
      predicting an inverse distance map for an actual boundary in the image set by blurring the actual boundary by a Gaussian function; and
      deriving the boundary from the inverse distance map.

2. The method of claim 1, wherein the deriving of the boundary from the predicted inverse distance map comprises thresholding the inverse distance map to obtain a binary boundary and subsequently extracting a medial axis of the binary boundary.

3. The method of claim 1, wherein the boundary computed by the convolutional neural network is an open boundary or a closed surface boundary.

4. The method of claim 1, wherein the convolutional neural network is configured to perform semantic image segmentation.

5. The method of claim 1, wherein the convolutional neural network implements a U-Net architecture comprising four layers comprising encoder blocks and decoder blocks,
   wherein each encoder block comprises a plurality of convolution filters, and
   wherein each decoder block comprises a plurality of deconvolution filters.

6. The method of claim 5, wherein the image set comprises a plurality of two-dimensional (2D) images,
   wherein the inverse distance map is predicted for a two-dimensional surface boundary about an area of interest in a 2D image of the plurality of 2D images, and
   wherein a two-dimensional boundary is inferred from the inverse distance map.

7. The method of claim 5, wherein the image set comprises a three-dimensional (3D) image volume,
   wherein the inverse distance map is predicted for a three-dimensional surface boundary about an area of interest in the 3D image volume, and
   wherein the three-dimensional surface boundary is inferred from the inverse distance map.

8. The method of claim 7, further comprising, prior to predicting the inverse distance map:
   generating the 3D image volume from a plurality of image slices obtained from a 2D imaging modality.

9. The method of claim 1, wherein the image set comprises a plurality of two-dimensional (2D) images,
   wherein the inverse distance map is predicted for a two-dimensional surface boundary about an area of interest in a 2D image of the plurality of 2D images, and
   wherein a two-dimensional boundary is inferred from the inverse distance map.

10. The method of claim 1, wherein the image set comprises a three-dimensional (3D) image volume,
    wherein the inverse distance map is predicted for a three-dimensional surface boundary about an area of interest in the 3D image volume, and
    wherein the three-dimensional surface boundary is inferred from the inverse distance map.

11. The method of claim 10, further comprising, prior to predicting the inverse distance map:
    generating the 3D image volume from a plurality of image slices obtained from a 2D imaging modality.

12. The method of claim 1, wherein the imaging modality is intracardiac echocardiography.

13. A method of training a convolutional neural network for use in determining a boundary about an area of interest in an image set, the method comprising:

annotating the image set to identify the boundary about the area of interest in the image set;

replicating an inverse distance map of the boundary for use as a ground truth by the convolutional neural network, wherein the replicating of the inverse distance map of the boundary is performed by blurring the boundary by a Gaussian function;

applying the convolutional neural network to the image set and the ground truth to predict the inverse distance map approximating the ground truth; and repeating the annotating, the replicating, and the applying until a desired level of accuracy has been achieved.

14. The method of claim 13, wherein the convolutional neural network is configured to minimize a mean squared error between the ground truth and the predicted inverse distance map.

15. A medical imaging arrangement comprising:

a processor comprising a convolutional neural network loaded into a memory of the processor, wherein the processor is configured to: obtain an image set and process the image set in the convolutional neural network, and wherein the convolutional neural network has been trained by predicting an inverse distance map for an actual boundary in the image set by blurring the actual boundary by a Gaussian function and deriving a computed boundary from the inverse distance map; and a user interface configured to display the computed boundary in a context of the image set.

\* \* \* \* \*